United States Patent [19]

Ooyama

[11] Patent Number: 4,458,013

[45] Date of Patent: Jul. 3, 1984

[54] METHOD FOR THE IMMUNOASSAY OF ELASTASE-1 AND A SET OF REAGENTS FOR SUCH IMMUNOASSAY

[75] Inventor: Toshiro Ooyama, Tokyo, Japan

[73] Assignee: Dainabot Kabushiki Kaisha, Tokyo, Japan

[21] Appl. No.: 267,396

[22] Filed: May 26, 1981

Related U.S. Application Data

[63] Continuation of Ser. No. 28,354, Apr. 9, 1979, abandoned.

[30] Foreign Application Priority Data

Jul. 5, 1978 [JP] Japan .................................. 53-81651

[51] Int. Cl.$^3$ ....................... G01N 33/50; C12Q 1/38; C12N 9/99
[52] U.S. Cl. ........................................... 435/7; 435/23; 435/184; 435/810; 436/528
[58] Field of Search .................... 435/7, 23, 24, 805, 435/184, 810; 23/230 B; 424/1, 1.5, 2, 12; 436/527, 531

[56] References Cited

PUBLICATIONS

Carballo et al., "Radio Immunoassay of Plasma Elastase", Chem. Absts., vol. 81, No. 19, p. 196, (1974), Abs. No. 116407y.

Araki, et al., "Immunological Determination of Serum Elastase by Its Inhibition of Hemagglutinin," Chem. Absts., vol. 78, No. 25, p. 111, (1973), Abs. No. 155818g.

Ooyama, et al., FEBS Letters, vol. 77, No. 1, (1977), pp. 61-64.

Ooyama, et al., Igaku No Ayumi, vol. 101, No. 1, (1977), pp. 22-23.

Rifkin, et al., "A Sensitive Assay for Elastase Employing Radioactive Elastin Coupled to Sepharose", Anal. Biochem., vol. 79, (1977), pp. 268-275.

Bergmeyer et al., Methods of Enzymatic Analysis, vol. 2, Academic Press, N.Y., (1974), pp. 1041-1045.

Ooyama, et al., "Radioimmunoassay of Pig Pancreatic Elastase", Chem. Absts., vol. 87, No. 5, (1977), p. 140, Abs. No. 34825j, p. 141, Abs. No. 34833k.

Ooyama, et al., Igaku No Ayumi, vol. 105, No. 3, (1978), pp. 91-97.

Primary Examiner—Esther M. Kepplinger
Attorney, Agent, or Firm—Birch, Stewart, Kolasch & Birch

[57] ABSTRACT

A method for the immunoassay of elastase-1 which comprises subjecting elastase-1 to be measured and a labelled antigen elastase-1, both having previously been treated with a synthetic elastase inhibitor, to a competitive reaction with anti-elastase-1 antibody, a kit of reagents for the immunoassay of elastase-1 which comprises a buffer liquid for immunoassay containing a synthetic elastase inhibitor, a labelled antigen elastase-1, a standard antigen elastase-1 and anti-elastase-1 antibody. The method and the kit of reagents for the immunoassay of elastase-1 are effectively utilized for diagnosis of pancreatic diseases, especially acute or chronic pancreatitis and cancer of the pancreas.

13 Claims, 4 Drawing Figures

Days after attack of pancreatitis (acute)

METHOD FOR THE IMMUNOASSAY OF ELASTASE-1 AND A SET OF REAGENTS FOR SUCH IMMUNOASSAY

This application is a continuation of copending application Ser. No. 28,354, filed on Apr. 9, 1979 now abandoned.

BACKGROUND OF THE INVENTION

This invention relates to a method and a kit of reagents for the measurement of elastase-1 useful for diagnosis of pancreatic diseases. More particularly, this invention relates to a method for the immunoassy of elastase-1, one of the pancreatic enzymes, contained in body fluid wherein a specific antigen-antibody reaction is used and also to a kit of reagents for such immunoassay.

In recent years, pancreatic diseases show a tendency to increase due to various reasons including diffusion of western-style meals and increase in the consumption of alcoholic drinks and in the number of peoples of advanced age and are now occupying an important position in clinical studies.

The pancreas is located in the deepest position of the peritoneal cavity and it is therefore difficult to find a pancreatic disease or observe the symptoms thereof by way of classical diagnostic methods such as palpation, inspection or auscultation and an X-ray examination. Thus, the development of an effective diagnostic method is strongly demanded in this field.

A blood amylase- or urinal amylase-measuring method is known as a diagnostic method for pancreatic diseases wherein body fluids of patients, chiefly, blood, urine, pancreatic juice, pleural dropsy and abdominal dropsy are used, and has been regarded for the past 20 years as a sole screening method and a definitive diagnostic method for pancreatic diseases. At present, however, this method is not considered to be important for the following reasons:

(1) In the case of chronic pancreatitis, the blood amylase value rarely becomes higher except at the peak stage thereof. On the other hand, the measurement of urinal amylase is of no practical significance and is not suited for diagnosis of chronic pancreatitis.

(2) In the case of acute pancreatitis, both blood amylase and urinal amylase show high values, but, after attack, the period within which such high values are shown is so short that diagnosis of the disease can not be made after expiration of the period.

(3) Since blood amylase is measured as a total quantity of two amylases, i.e. those of salivary and pancreatic origins, the measurement per se of amylase is not deemed as a peculiar testing method for pancreatic diseases.

In view of the foregoing reasons, the development of a method for measuring pancreatic enzymes other than amylase is necessary for diagnosis of pancreatic diseases.

Human pancreas or pancreatic juice contains elastase in addition to amylase. The "elastase" is a general term for proteases capable of cleaving elastin, i.e. elastic fibers in connective tissues and is widely distributed in pancreas, luecocytes, thrombocytes, spleen, etc. Two kinds of pancreatic elastase are known which are different from each other in respect of physicochemical and enzymological properties as well as antigenic characteristics. Generally, anionically charged elastase existing in a very small proportion is defined as elastase-1 and cationically charged elastase existing in a very large proportion as elastase-2. These enzymes are quite different in physiological function and have no cross-immunity. Elastase-1 alone is dealt with in the present invention as a pancreatic elastase to be measured for diagnosis of pancreatic diseases. This enzyme is known to have a molecular weight of 30,500, a serum level of 2 ng/ml and a pancreatic juice level of 1~30 μg/ml and shows a clear contrast to the other elastase-2 having a molecular weight of 24,500 and a serum level of 71 ng/ml and a pancreatic juice level of 500 μg/ml.

Some attempts have been made hitherto for the purpose of measuring the concentration of blood elastase-1 by way of the enzymatic activity-measuring method. However, the measurement of the quantity of elastase-1 by taking advantage of its enzymatic activity was extremely difficult for the following reasons:

(1) Because the content of pancreatic elastase-1 i. blood is very small (2 ng/ml), the measurement of the pancreatic elastase-1 by colorimetry is extremely difficult even in the case of using succinyl trialanyl p-nitroanilide (the minimum detection sensibility: 50 ng/ml), the most sensitive synthetic substrate at present.

(2) As elastase inhibitors are present at a concentration of about $10^3$ times as much as elastase-1 in blood, the measurement of elastase-1 as enzymatic activity is theoretically impossible.

(3) No assurrance is given for peculiarity in the enzymatic activity-measuring method wherein a substrate is used, since the method is also influenced by enzymes other than elastase-1.

Under the circumstances described above, it was quite impossible to measure the quantity of elastase-1 by way of the conventional enzymatic activity-measuring method. Consequently, there is a great demand for developing a new method for effectively and precisely measuring elastase-1 in place of the conventional enzymatic activity-measuring method, especially in the field of diagnosis of pancreatic diseases.

BRIEF SUMMARY OF THE INVENTION

Accordingly, it is an object of the present invention to provide a method for the immunoassay of elastase-1 applicable to diagnosis of pancreatic diseases.

It is another object of the present invention to provide a method for the immunoassay of elastase-1 contained in a trace amount in various body fluids without accompanying drawbacks seen in the conventional enzymatic activity-measuring method.

It is still another object of the present invention to provide a set of reagents for the immunoassay of elastase-1 applicable to diagnosis of pancreatic diseases.

Other objects, features and advantages of the present invention will become apparent as the description proceeds.

DETAILED DESCRIPTION OF THE INVENTION

Figure 1:
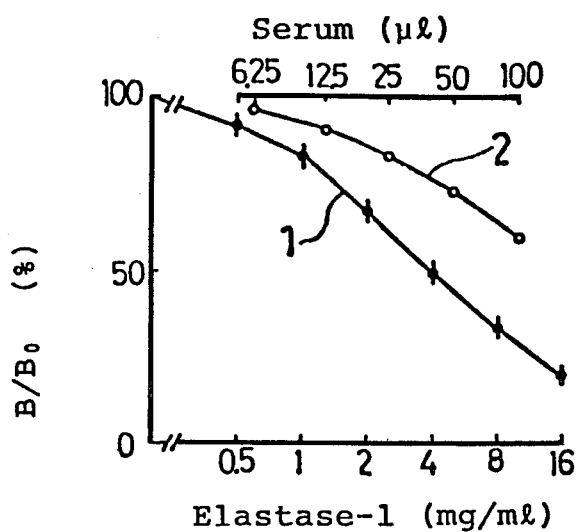
FIG. 1 is a graph showing a result of radioimmunoassay according to the method of this invention obtained in Example 2.

As a result of extensive research made to overcome the drawbacks of the conventional enzymatic activity-measuring method and to develop a new method for effectively measuring elastase-1 contained in various body fluids, it has now been found that elastase-1 can be measured immunologically without being badly influenced by natural elastase inhibitors when elastase-1 containing a given proportion of a labelled antigen elastase-1, both previously treated with a synthetic elastase inhibitor, is reacted with anti-elastase-1 antibody and the quantity of the elastase-1 is calculated by measuring the activity of the labelling agent in the antibody-bound labelled antigen on the basis of standard values plotted previously with respect to the standard antigen. The present invention is based on the above finding.

In accordance with one embodiment of the present invention, there is provided a method for the immunoassay of elastase-1, characterized by subjecting a sample containing elastase-1 to be measured and a given proportion of a labelled antigen elastase-1, both having previously been treated with a synthetic elastase inhibitor, to a competitive reaction with anti-elastase-1 antibody, separating the antibody-bound labelled antigen from the free labelled antigen, measuring the activity of the labelling agent in either or both of the fractions, and calculating the quantity of the elastase-1 on the basis of standard values plotted previously with respect to the standard antigen according to the treatment in a similar manner.

Any of the labelling agents conventionally used in biochemical treatments can be used as a labelling agent for preparing the labelled antigen elastase-1. Illustrative of such labelling agents are, for example, radioisotopes such as $^{125}I$ and $^{131}I$, enzymes such as alkaline phosphatase, peroxidase, and lysozyme, and fluorescent substances such as fluorescein and rhodamine dyes. Amont these labelling agents, radioisotopes are conveniently used in the method of this invention whereby the measurement of elastase-1 is performed according to radioimmunoassay.

The labelling treatment per se of the antigen with such labelling agent is carried out according to a known conventional method, for example, Hunter and Greenwood's Chloramine T method [Hunter and Greenwood: Nature 194 495 (1964)].

Examples of the synthetic elastase inhibitor include diisopropyl fluorophosphate (referred to herein simply as DFP), phenylmethanesulfonyl fluoride and p-chloromercuribenzoates. The use of DFP is preferable in the present invention.

The method of the present invention is fundamentally different from the conventional immunoassay in the point that the labelled antigen and the standard antigen of the present invention have to be treated previously with the synthetic elastase inhibitor for antigen elastase-1 such as DFP.

In case elastase-1 in body fluid such as blood is measured according to a conventional method by way of immunoassay, natural elastase inhibitors contained in the body fluid such as serum are bound to the labelled and standard antigens whereby a part or all of the antigenic characteristics are lost and the immunochemical reaction is significantly disturbed. In the past, therefore, the accurate determination of elastase-1 could not be made according to the conventional immunochemical method. Contrary to this, natural elastase inhibitors contained in body fluid are not bound to elastase-1 in the method of this invention wherein the labelled antigen and the standard antigen are previously masked with the synthetic elastase inhibitor such as DFP. In addition, the antigenic characteristics of elastase-1 is not at all modified by the synthetic elastase inhibitor previously bound to elastase-1, thus making it possible to measure the concentration of elastase-1 in body fluid with high accuracy and sensitivity.

The separation of the antibody-bound labelled antigen from the free labelled antigen is conducted according to any of the conventional methods including the solid phase method wherein Sepharose gel, glass pieces or silicone pieces are used, the sandwich method and the double antibody method wherein the free labelled antigen remaining in the liquid by the action of, for example, a certain animal's normal serum and another animal's γ-globulin antiserum against the certain animal. Various normal sera and antisera of cattles such as rabbit, goat, horse, pig, cow, guinea pig, rat, sheep and poultry may be used for the double antibody method but a combination of normal rabbit serumand goat anti-rabbit γ-globulin antiserum is preferably used in this invention. The latter mentioned antiserum is sometimes called "second antiserum" in the double antibody method.

Usually, the antigen-antibody reaction between the labelled or standard elastase-1 (or a sample to be measured) pretreated with the synthetic inhibitor such as DFP and the anti-elastase-1 antibody is conducted by incubating a mixture of these in a buffer liquid at 4° C. for 48 hours and the subsequent separation treatment according to the double antibody method is conducted by adding a combination of normal serum and a second antiserum to the above antigen-antibody reaction mixture, incubating the mixture at 4° C. for 24 hours and then centrifuging for 30 minutes at a rotating speed of for example, about 3000 r.p.m.

In case a radioisotope such as a radioactive iodine isotope is used as labelling agent, the determination of the antibody-bound labelled antigen elastase-1 separated as a precipitate from the free labelled antigen in the double antibody method can be made by measuring radioactivity of the precipitate, for example, with a γ-counter. The mode of this measurement is referred to as radioimmunoassay. In case a fluorescent substance is used as labelling agent, the antibody-bound labelled antigen elastase-1 may be separated, for example, by way of chromatography and determined by measuring the intensity of fluorescence.

Prior to measuring the activity, e.g. radioactivity, of the precipitate obtained from a sample, the method is first carried out, e.g. by using a DFP-treated standard elastase-1 to prepare a standard curve for determination by plotting measured values on a graph. The method is then carried out using a sample, i.e. a body fluid such as serum to measure the activity of the labelling agent in the precipitate. The quantity of elastase-1 contained in the sample can easily be calculated from the measured values by converting them on the basis of the standard values previously plotted as a standard curve on a graph.

In accordance with another embodiment of the present invention, there is provided a kit of reagents for the immunoassay of elastase-1 which comprises (1) a buffer liquid for immunoassay containing a synthetic inhibitor, (2) a labelled antigen elastase-1, (3) a standard antigen elastase-1 and (4) an anti-elastase-1 antibody.

Any of the buffer solutions utilizable for immunochemical treatments can be used as the buffer liquid (1) for the present invention, so far as it contains the above described synthetic elastase inhibitor. A labelling agent of the types as described hereinbefore can also be used for the preparation of the ingredient (2). Purified human pancreatic elastase-1 obtained, for example, by Feinstein et al. method [Feinstein, Hofstein, Koifman & Sokolovsky: Eur. J. Biochem. 43 569(1974)] or Cuatrecasas et al. method [Cuatrecasas, Wilcheck & Anfinsen: Proc. Natl. Acad. Sci. U.S.A. 61 635 (1968)] can be used for the standard labelled antigen elastase-1 (3). The anti-elastase-1 antibody (4) is derived from the standard antigen elastase-1 (3) according to the conventional immunological treatments.

If desired, the above set of reagents may involve the following additional reagents:

(5) a normal animal-1 serum (6) an anti-animal-1 γ-globulin antibody animal-2 serum which are necessary in the double antibody method for the separation of the antibody-bound labelled antigen elastase-1 from the free labelled antigen elastase-1.

Animal-1 and animal-2 referred to above are selected from cattles and poultry such as rabbit, rat, goat, horse, cow, pig, sheep, guinea pig, hen, etc., with the proviso that the animal-1 is different from the animal-2.

These normal serum and antibody serum can be prepared according to the method known per se in the field of immunochemistry. In the double antibody method, the reagent (6) is sometimes called "second antibody ( for antiserum)" for distinguishing itself from the reagent (4).

These reagants are usually stored in a freezer maintained at $-20°$ C. or lower to prevent any denaturation.

The method of this invention does not rely on enzymatic activity of elastase-1 but takes advantage of the antigen-antibody reaction. Thus, the present invention is advantageous particularly in that it is free from bad influence of natural elastase inhibitors existing in serum and exerts peculiarity based on the immunological principle. The method of this invention is exclusively directed to the immunoassay of human pancreatic elastase-1 because this elastase-1 shows no cross-immunity with human pancreatic elastase-2, rat pancreatic elastase and pig pancreatic elastase.

Further, the method of this invention can be applied advantageously to diagnosis of various pancreatic diseases as it concerns the immunoassay of one of the enzymes peculiar to pancreas. Since the immunoassay of elastase-1 according to the present invention can be made with an amount as small as 0.1 ml of a physiological fluid specimen such as blood or urine easily extracted from living body, the method serves as a simple screening test for diagnosis of pancreatic diseases. In addition, the method of this invention is peculiar to elastase-1 and is of particular significance in that the method can be utilized more effectively for a definitive diagnosis of pancreatic diseases than the existing method for measuring amylase activity. For example, the level of amylase measured in body fluid shows a value within the normal range even in case of carcinoma of the pancreas. Contrary to this, the level of elastase-1 measured in body fluid shows a very high value in case of carcinoma of the pancreas and this tendency is significant especially at the early stage thereof. Thus, the immunoassay of elastase-1 is especially valuable for discovery of carcinoma of the pancreas at the early stage thereof. On the other hand, the level of elastase-1 shows an exceptionally low value in case of chronic pancreatitis while that of amylase is within the normal range. In case of acute pancreatitis, both elastase-1 and amylase show a high level. However, the level of amylase relatively soon drops within the normal range with the lapse of time while the level of elastase-1 is responsible to the condition of disease irrespective of the lapse of time. Consequently, the diagnosis of chronic or acute pancreatitis is rather easier in case of the immunoassay of elastase-1.

The method and the set of reagents for the immunoassay of elastase-1 according to the present invention are thus valuable for definitive diagnosis of pancreatic diseases.

The present invention will now be illustrated in more detail by way of Examples and Reference Examples. In Example 1, the method of preparing the individual reagents is illustrated. In Example 2, the readioimmunoassay off elastase-1 was performed by using $^{125}I$ as labelling agent and adopting the double antibody method for separating the antibody-bound labelled antigen elastase-1 from the free labelled elastase-1. It is to be construed that the present invention is not limited to the specific embodiments illustrated in these Examples.

EXAMPLE 1

(A) Purification of human pancreatic elastase-1

The purification treatment was conducted according to Feinstein et al. method [Eur. J. Biochem. 43 569 (1974)]. At the first stage of the purification treatment affinity chromatography was applied wherein Lima bean trypsin inhibitor Sepharose (LBIT Sepharose) prepared by coupling Lima bean trypsin inhibitor with Br-CN activated Sepharose 4B was used. Concentrated human pancreatic juice was passed through a column packed with the Sepharose gel which had been equilibrated with 50-nM Tris-HCl buffer [pH 8 (20-mM $CaCl_2$ contained)] and the gel was washed with the above buffer until UV-absorption at 280 nm of the eluate reached almost zero. An elastase-1 active fraction was then eluted with a 0.1-M acetic acid solution [pH 3.0 (20-mM $CaCl_2$ contained)]. The eluate was then passed through a column charged with SP Sephadex C-50 gel equilibrated with a 20-mM sodium acetate buffer having a pH value of 4.0 and the adsorbed fraction was then eluted with the elution buffer while adding thereto edible salt increasing at a linear gradient thereby elastase-1 was isolated.

The purified elastase-1 showed a single band in a analytical grade polyacrylamide gel electrophoresis.

(B) Preparation of anti-elastase-1 antiserum

In a 50-mM phosphate buffer having a pH value of 7.4 was dissolved the purified elastase-1 obtained in the preceding step (A), thereby forming a solution having a concentration of 1 mg/ml. One ml of this solution was mixed with an equiamount of Freund complete adjuvant to form an emulsion with which a white rabbit was injected 5 times in all at biweekly intervals. At 10 days after the final injection, the blood was collected and the serum was separated and inactivated at 56° C. for 30 minutes.

(C) Preparation of $^{125}$I-labelled antigen elastase-1

$^{125}$I-antigen elastase-1 was prepared according to the Chloramine T method. The reagent having a radiological specific activity of 100~200 μCi/μg is preferable.

In case DFP-treated $^{125}$I-antigen elastase-1 is prepared, the labelled antigen was subjected, after the labelling treatment, to a column chromatography using Sephadex gel whereby a buffer used for the separation of the labelled antigen from unreacted $^{125}$I (the above mentioned 50-mM phosphate buffer having a pH value of 7.4) in which DFP had been dissolved to have a concentration of 1-mM was used. By this treatment, elastase-1 was converted into an enzymatically inactive form. The bonding of DFP-treated elastase-1 is irreversible.

(D) Preparation and storage of a set of reagents for immunoassay (1) A buffer liquid for radioimmunoassay A 50-mM phosphate buffer liquid containing 0.2% cow serum albumin, 0.01% sodium azide and 1-mM DFP (pH 7.4).

(2) Labelled antigen elastase-1

After the labelling treatment, the antigen was immediately diluted with the buffer liquid (1) to have a concentration of 10,000 cpm/0.1 ml, placed in a plastic vial at −20° C. and tightly sealed for storage.

(3) Standard antigen elastase-1

The purified elastase-1 obtained in the step (A) was dissolved in a 50-mM phosphate buffer liquid described in the step (B) to have a concentration of 1 mg/ml. This solution was adjusted with the buffer liquid (1) to have a concentration of 256 ng/ml, placed in a plastic vial at −20° C. and tightly sealed for storage. On dilution with the buffer liquid (1), elastase-1 was reacted with DFP contained in the buffer liquid to form DFP-treated elastase-1

(4) Antiserum

The anti-elastase-1 antiserum obtained in the step (B) was diluted with the buffer liquid (1) to 1:100, placed in a plastic vial at −20° C. and tightly sealed for storage.

(5) Normal rabbit serum.

A serum obtained from normal rabbit was placed in a plastic vial at −20° C. and tightly sealed for storage.

(6) Second antibody (or antiserum)

Goat anti-rabbit γ-globulin antiserum was properly diluted with the buffer liquid (1), placed in a plastic vial at 3120° C. and tightly sealed for storage.

(7) Human pool serum

The serum was placed in a plastic vial at −20° C. and tightly sealed for storage.

EXAMPLE 2

In this example, dilution of the reagents was made by using the buffer liquid (1) unless otherwise indicated.

In a glass test tube of 9 mm × 75 mm were placed in the written order, 0.1 ml of the antiserum (1:80,000), 0.1 ml of the labelled antigen (10,000 cpa), 0.1 ml of the standard antigen or a test serum (a sample containing elastase-1 to be measured) and 0.4 ml of the buffer liquid to make the total volume to 0.7 ml. The mixture was allowed to stand stationary at 4° C. for 48 hours. Then, 0.1 ml of the normal rabbit serum and 0.1 ml of goat anti-rabbit γ-globulin antiserum (1:20) were added and the whole was allowed to stand stationary for 24 hours at 4° C. The mixture was then subjected to centrifugal separation conducted at a rotation speed of 3000 r.p.m. for 30 minutes. After discarding the supernatant liquid, the precipitate was collected and the radioactivity thereof was measured with a γ-counter.

FIG. 1 shows a result of the radioimmunoassay thus performed wherein a curve 1 stands for a standard curve obtained with respect to the standard antigen and each spot for an average value of 5 experiments ± a standard error. The abscissa stands for the quantity of elastase-1, while the ordinate for a ratio by percentage of B/T (B is the number of counts of antibody-bound labelled antigen while T is the number of total counts) to $B_o/T$ ($B_o$ is the number of counts of the antibody-bound labelled antigen when the amount of the standard antigen added is zero). A curve 2 in FIG. 1 stands for a replacement curve obtained with respect to the pool serum whereby the quantity of the pool serum added is also shown in the abscissa. As is evident from FIG. 1, the method of this invention is excellent in stability and sensibility (the minimum detectable level: about 0.5 ng/ml) and the results obtained are reproducible. Data on stability ($X_{0.5}$: the quantity of elastase-1 sufficient to product 50% $B/B_0$ replacement on the standard curve), sensibility represented by the minimum detectable level (MDL in terms of ng/ml), and reproducibility (elastase-1 content in pool serum) are shown in Table 1 below.

TABLE 1

| Exp. No. | $X_{0.5}$ (ng/ml) | MDL (ng/ml) | Content of elastase-1 in pool serum (ng/ml) |
|---|---|---|---|
| 1 | 4.0 | 0.37 | 2.5 |
| 2 | 4.0 | 0.7 | 2.8 |
| 3 | 4.0 | 0.45 | 2.7 |
| 4 | 4.5 | 0.63 | 3.0 |
| 5 | 4.3 | 0.25 | 2.0 |

The method of this invention is about 100 times as much in sensibility as the conventional enzymatic activity-measuring method.

EXAMPLE 3

(Referential Example 1)

Figure 2:
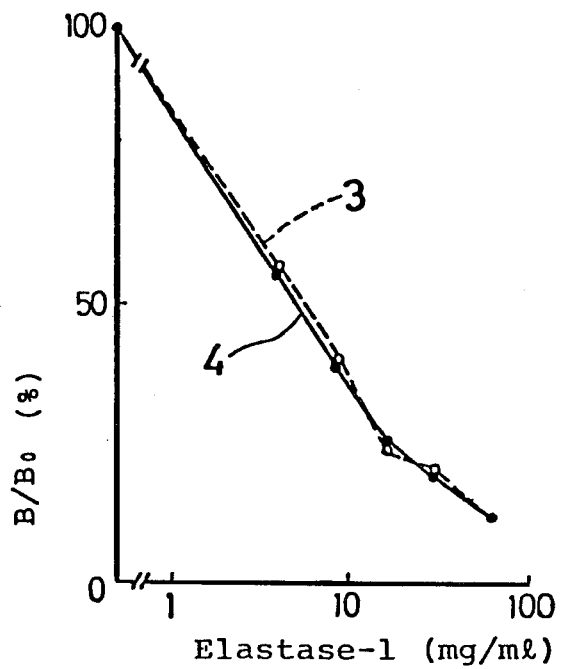
FIG. 2 is a graph showing standard curves obtained in the case of using DFP-treated elastase-1 and untreated elastase-1.

With a view to investigating how the antigenic characteristics of elastase-1 are changed by the treatment with DFP, standard curves were prepared with respect to both DFP-treated antigen and untreated antigen and compared with each other, the result being shown in FIG. 2.

In FIG. 2, a curve 3 is a standard curve obtained with respect to the DFP-treated antigen while a curve 4 a standard curve obtained with respect to the untreated antigen. As is evident from FIG. 2, no change is found in antigenic characteristics of elastase-1 by the bonding of DFP to elastase-1.

EXAMPLE 4

(Referential Example 2)

Figure 3:
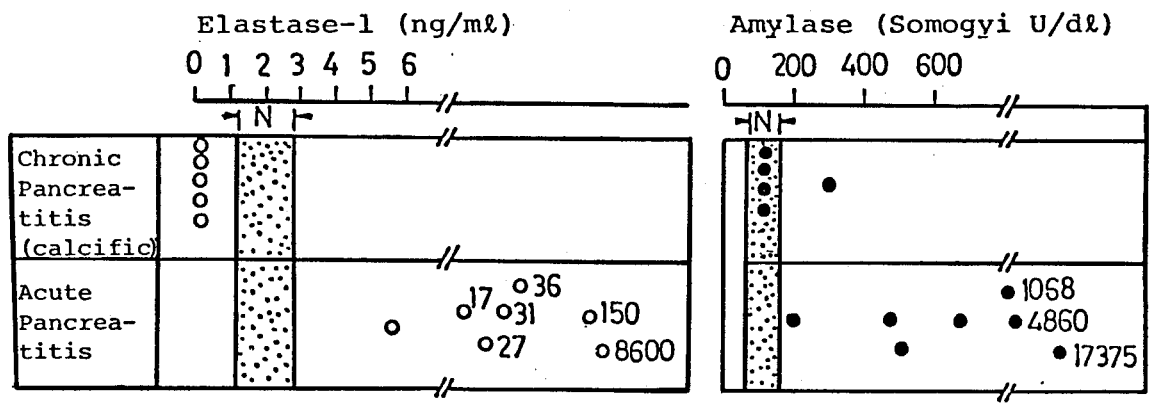
FIG. 3 is a diagram showing serum elastase-1 values and serum amylase values in chronic and acute pancreatitis.
Figure 4:
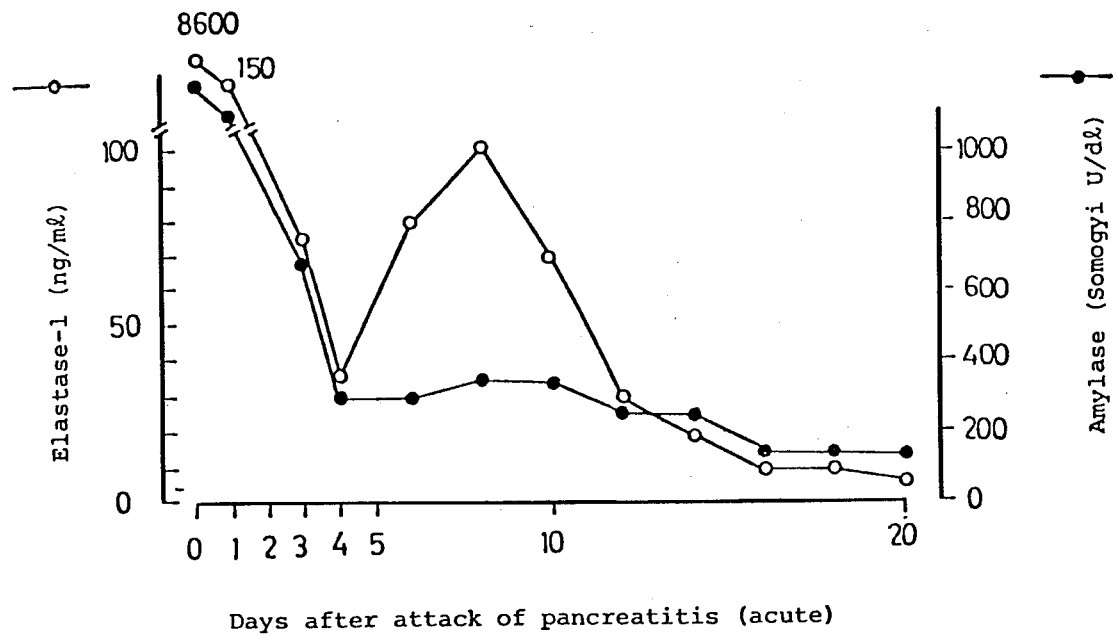
FIG. 4 is a graph showing changes of serum elastase-1 values and serum amylase values with the lapse of time in chronic and acute pancreatitis.

The serum elastase-1 levels and the serum amylase levels measured with respect to patients suffering from chronic pancreatitis (calcific) and acute pancreatitis are shown in FIG. 3. The area N in FIG. 3 stands for the normal range of the levels for elastase-1 or amylase. In case of acute pancreatitis, changes in the levels of elastase-1 and amylase with the lapse of time are graphically shown in FIG. 4. The measurements of serum elastase-1 by way of the immunoassay is significantly useful for diagnosis of pancreatitis as compared with the measurement of serum amylase by way of the enzymatic activity-measuring method, especially in the following points:

(a) In case of chronic pancreatitis (calcific), the level of elastase-1 shows an extremely low value while that of amylase is within the normal range in the majority of the cases. Thus, diagnosis of chronic pancreatitis is easily made by measuring the level of elastase-1.

(b) In case of acute pancreatitis, both elastase-1 and amylase show a high level. However, the level of amylase soon drops within the normal range with the lapse of time in contrast to the level of elastase-1 kept at a high level for a relatively long period of time.

It is understood that the preceding representative examples may be varied within the scope of the present invention, both as to the reagents and immunoassay conditions, by one skilled in the art to achieve essentially the same results.

As many widely different embodiments of this invention may be made without departing from the spirit and scope thereof, it is to be understood that this invention is not limited to the specific embodiments thereof except as defined in the appended claims.

What is claimed is:

1. A method for the immunoassay of elastase-1 comprising the steps of: subjecting a sample containing immunologically active enzymatically inactive elastase-1 to be measured and a given quantity of standard immunologically active enzymatically inactive labelled antigen elastase-1, both having been previously reacted with a synthetic elastase inhibitor selected from the group consisting of diisopropyl fluorophosphate, phenylmethanesulfonyl fluoride, and p-chloromercuribenzoates to prevent the enzymatic activity of elastase-1, to a competitive reaction with an anti-elastase-1 antibody; separating the antibody-bound labelled antigen elastase-1 and the free labelled antigen elastase-1 from the reaction mixture; measuring the activity of the labelling agent in either or both of the fractions; and comparing the quantity of the elastase-1 in the sample with standard values to determine the amount of elastase-1 in said sample to be measured.

2. A method according to claim 1, wherein said labelling agent is a radioisotope.

3. A method according to claim 2, wherein the radioisotope is $^{125}I$.

4. A method according to claim 1, wherein the sample is blood.

5. A method for the diagnosis of pancreatic diseases which comprises performing the method of claim 1, wherein the sample containing elastase-1 to be measured is from a human patient being diagnosed for pancreatic disease.

6. A method for the immunoassay of elastase-1 according to claim 1, wherein said standard values have been previously plotted with respect to said standard antigen elastase-1.

7. A method according to claim 1, wherein said labelling agent is selected from the group consisting of radioisotopes, enzymes, fluorescent substances and dyes.

8. A kit of reagents for the immunoassay of elastase-1 which comprises:
   (1) a buffer liquid for immunoassay containing a synthetic elastase inhibitor selected from the group consisting of diisopropyl fluorophosphate, phenylmethanesulfonyl fluoride, and p-chloromercuribenzoates capable of reacting with elastase-1 to form an immunologically active enzymatically inactive reaction product;
   (2) a labelled antigen elastase-1 which is labelled with a labelling agent;
   (3) a standard antigen elastase-1; and
   (4) an anti-elastase-1 antibody which is reactive with said labelled antigen elastase-1 and said standard antigen elastase-1 wherein ingredients (1)-(4) are present in an amount sufficient to perform an immunoassay of elastase-1.

9. A kit of reagents according to claim 8, and further including (5) a normal animal-1 serum and (6) and anti-animal-1 γ-globulin antibody animal-2 serum for use in a double antibody method.

10. A kit of reagents according to claim 9, wherein said normal animal-1 serum is normal rabbit serum and said anti-animal-1 γ-globulin antibody animal-2 serum is goat anti-rabbit γ-globulin antiserum.

11. A kit of reagents according to claim 8, wherein said labelling agent is a radioisotope.

12. A kit of reagents according to claim 11, wherein said radioisotope is $^{125}I$.

13. A kit according to claim 8, wherein said elastase-1 is labelled with a labelling agent selected from the group consisting of radioisotopes, enzymes, fluorescent substances and dyes.

* * * * *